(12) United States Patent
Rykhus, Jr. et al.

(10) Patent No.: US 8,747,386 B2
(45) Date of Patent: Jun. 10, 2014

(54) ANASTOMOSIS DEVICE AND RELATED METHODS

(75) Inventors: Robert L. Rykhus, Jr., Edina, MN (US); Richard G. Rhode, St. Louis Park, MN (US)

(73) Assignee: AMS Research Corporation, Minnetonka, MN (US)

( * ) Notice: Subject to any disclaimer, the term of this patent is extended or adjusted under 35 U.S.C. 154(b) by 95 days.

(21) Appl. No.: 13/328,729

(22) Filed: Dec. 16, 2011

(65) Prior Publication Data

US 2012/0157974 A1    Jun. 21, 2012

Related U.S. Application Data

(60) Provisional application No. 61/423,739, filed on Dec. 16, 2010.

(51) Int. Cl.
*A61M 1/00* (2006.01)
*A61M 25/00* (2006.01)

(52) U.S. Cl.
USPC ........ 604/524; 604/95.04; 604/525; 604/528; 604/540

(58) Field of Classification Search
USPC ............... 604/95.04, 525, 528, 540, 541, 544
See application file for complete search history.

(56) References Cited

U.S. PATENT DOCUMENTS

| | | | |
|---|---|---|---|
| 4,368,736 A | 1/1983 | Kaster | |
| 4,553,542 A | 11/1985 | Schenck et al. | |
| 4,701,162 A | 10/1987 | Rosenberg | |
| 4,705,502 A | 11/1987 | Patel | |
| 4,792,330 A | 12/1988 | Lazarus et al. | |
| 4,848,367 A | 7/1989 | Avant et al. | |
| 4,873,977 A | 10/1989 | Avant et al. | |
| 4,909,785 A | 3/1990 | Burton et al. | |
| 4,911,164 A | 3/1990 | Roth | |
| 4,932,956 A | 6/1990 | Reddy et al. | |
| 4,932,958 A | 6/1990 | Reddy et al. | |
| 4,946,449 A | 8/1990 | Davis, Jr. | |
| 5,047,039 A | 9/1991 | Avant et al. | |
| 5,112,306 A | 5/1992 | Burton et al. | |
| 5,123,908 A | 6/1992 | Chen | |
| 5,152,772 A | 10/1992 | Sewell, Jr. | |
| 5,306,226 A | 4/1994 | Salama | |
| 5,322,501 A | 6/1994 | Mahmud-Durrani | |

(Continued)

FOREIGN PATENT DOCUMENTS

| | | |
|---|---|---|
| WO | WO 92/04869 | 4/1992 |
| WO | WO 96/07447 | 3/1996 |

(Continued)

OTHER PUBLICATIONS

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

(Continued)

*Primary Examiner* — Melanie Hand
(74) *Attorney, Agent, or Firm* — Gregory L. Koeller

(57) ABSTRACT

An anastomosis device that includes a catheter body is provided. A distal end portion of the catheter can include a spring device to prevent the formation of blood clots and to improve the flow of urine out of the catheter. The device may be used, for example, in performing procedures such as a vesicourethral anastomosis in association with a radical prostatectomy, or with an end-to-end urethral anastomosis.

15 Claims, 4 Drawing Sheets

(56) References Cited

U.S. PATENT DOCUMENTS

| | | |
|---|---|---|
| 5,454,825 A | 10/1995 | Van Leeuwen et al. |
| 5,540,701 A | 7/1996 | Sharkey et al. |
| 5,545,171 A | 8/1996 | Sharkey et al. |
| 5,599,321 A | 2/1997 | Conway et al. |
| 5,643,248 A | 7/1997 | Yoon |
| 5,653,690 A | 8/1997 | Booth et al. |
| 5,695,504 A | 12/1997 | Gifford, III et al. |
| 5,707,380 A | 1/1998 | Hinchliffe et al. |
| 5,833,698 A | 11/1998 | Hinchliffe et al. |
| 5,836,967 A | 11/1998 | Schneider |
| 5,931,842 A | 8/1999 | Goldsteen et al. |
| 5,951,576 A | 9/1999 | Wakabayashi |
| 5,964,791 A | 10/1999 | Bolmsjo |
| 6,024,748 A | 2/2000 | Manzo et al. |
| 6,119,045 A | 9/2000 | Bolmsjo |
| 6,149,667 A | 11/2000 | Hovland et al. |
| 6,193,734 B1 | 2/2001 | Bolduc et al. |
| 6,238,368 B1 | 5/2001 | Devonec |
| 6,254,570 B1 | 7/2001 | Rutner et al. |
| 6,280,460 B1 | 8/2001 | Bolduc et al. |
| 6,299,598 B1 | 10/2001 | Bander |
| 6,302,905 B1 | 10/2001 | Goldsteen et al. |
| 6,391,039 B1 | 5/2002 | Nicholas et al. |
| 6,416,545 B1 | 7/2002 | Mikus et al. |
| 6,440,146 B2 | 8/2002 | Nicholas et al. |
| 6,447,533 B1 | 9/2002 | Adams |
| 6,461,367 B1 | 10/2002 | Kirsch et al. |
| 6,485,496 B1 | 11/2002 | Suyker et al. |
| 6,494,908 B1 | 12/2002 | Huxel et al. |
| 6,520,974 B2 | 2/2003 | Tanner et al. |
| 6,530,932 B1 | 3/2003 | Swayze et al. |
| 6,558,349 B1 | 5/2003 | Kirkman |
| 6,562,024 B2 | 5/2003 | Alvarez de Toledo et al. |
| 6,565,579 B2 | 5/2003 | Kirsch et al. |
| 6,599,311 B1 | 7/2003 | Biggs et al. |
| 6,602,243 B2 | 8/2003 | Noda |
| 6,689,147 B1 | 2/2004 | Koster, Jr. |
| 6,695,787 B2 | 2/2004 | Hogendijk et al. |
| 6,695,832 B2 | 2/2004 | Schon et al. |
| 6,702,825 B2 | 3/2004 | Frazier et al. |
| 6,719,709 B2 | 4/2004 | Whalen et al. |
| 6,719,749 B1 | 4/2004 | Schweikert et al. |
| 6,726,697 B2 | 4/2004 | Nicholas et al. |
| 6,740,098 B2 | 5/2004 | Abrams et al. |
| 6,746,456 B2 | 6/2004 | Xiao |
| 6,746,472 B2 | 6/2004 | Frazier et al. |
| 6,821,283 B2 | 11/2004 | Barzell et al. |
| 7,481,793 B2 | 1/2009 | Abrams et al. |
| 7,717,928 B2 | 5/2010 | Copa et al. |
| 7,771,443 B2 | 8/2010 | Copa et al. |
| 2001/0049492 A1 | 12/2001 | Frazier et al. |
| 2002/0002363 A1 | 1/2002 | Urakawa et al. |
| 2002/0087176 A1 | 7/2002 | Greenhalgh |
| 2002/0177902 A1 | 11/2002 | Rioux et al. |
| 2003/0069629 A1 | 4/2003 | Jadhav et al. |
| 2003/0199817 A1 | 10/2003 | Thompson et al. |
| 2003/0208183 A1 | 11/2003 | Whalen et al. |
| 2003/0229364 A1 | 12/2003 | Seiba |
| 2004/0006331 A1 | 1/2004 | Shchervinsky |
| 2004/0078047 A1 | 4/2004 | Nicholas et al. |
| 2004/0087995 A1 | 5/2004 | Copa et al. |
| 2004/0167547 A1 | 8/2004 | Besne et al. |
| 2005/0059958 A1 | 3/2005 | Lessard et al. |
| 2005/0070938 A1 | 3/2005 | Copa et al. |
| 2005/0131431 A1 | 6/2005 | Copa et al. |
| 2005/0192602 A1 | 9/2005 | Manzo |
| 2005/0251155 A1 | 11/2005 | Orban, III |
| 2005/0288764 A1 | 12/2005 | Snow et al. |
| 2006/0200178 A1 | 9/2006 | Hamel et al. |
| 2006/0206122 A1 | 9/2006 | Copa et al. |
| 2006/0264985 A1 | 11/2006 | Copa et al. |
| 2007/0005095 A1 | 1/2007 | Osborne et al. |
| 2007/0219584 A1 | 9/2007 | Copa et al. |

FOREIGN PATENT DOCUMENTS

| | | |
|---|---|---|
| WO | WO 96/16606 | 6/1996 |
| WO | WO 99/16359 | 4/1999 |
| WO | WO 99/21490 | 5/1999 |
| WO | WO 99/21491 | 5/1999 |
| WO | WO 99/58081 | 11/1999 |
| WO | WO 04/000135 | 12/2003 |
| WO | WO 04/000137 | 12/2003 |
| WO | WO 04/000138 | 12/2003 |
| WO | WO 2004/034913 | 4/2004 |
| WO | WO 2007/013070 | 2/2007 |

OTHER PUBLICATIONS

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

Hruby, G.W., "Comparison of a Novel Tissue Apposing Device and Standard Anastomotic Technique for Vesicourethral Anastomses," Journal of Endourology, vol. 20, Supplement 1 VP12-02 p. A69 (abstract) Aug. 2006.

Hruby, G.W., "Comparison of a Novel Tissue Apposing Device and Standard Anastomotic Technique for Vesicourethral Anastomses," Journal of Urology, vol. 175, No. 4, p. 347, Apr. 2006.

ANASTOMOSIS DEVICE AND RELATED METHODS

PRIORITY CLAIM AND RELATED APPLICATION

The present application claims the benefit of U.S. Provisional Application No. 61/423,739 filed Dec. 16, 2010, and entitled "ANASTOMOSIS DEVICE AND RELATED METHODS", which is incorporated herein in its entirety by reference.

FIELD OF THE INVENTION

The present invention generally relates to urinary catheters. More specifically, the present invention is directed to a urinary catheter that includes a clot prevention component located at a distal treatment end so as to facilitate fluid removal during urological procedures.

BACKGROUND OF THE INVENTION

Urinary catheters are well known devices that allow medical professionals to access targeted sites within a patient's urinary tract. Depending upon the particular procedure to be performed, the urinary catheter can facilitate the delivery of treatment devices or medicants or can provide a drainage function whereby fluid can be removed from the urinary tract. One procedure in which a urinary catheter can function to both deliver treatment devices and provide for fluid drainage is in a radical prostatectomy in which a surgeon removes all or most of a patient's prostate. Because the urethra travels through the prostate immediately before reaching the bladder, the upper part of the urethra is removed in the surgery. The procedure leaves a severed urethral stump and a severed bladder neck. To restore proper urinary functions, the bladder and the urethra must be reconnected.

Conventionally, a surgeon may execute delicate suturing operations with tiny, fine needles to reconnect these anatomical bodies. Installation of sutures, however, with a needle, to connect the severed tissues, can be a difficult and often technique-sensitive task. Many factors can make this task difficult, including a very small amount of tissue to work with (at the urethral stump and at the bladder neck), proximal ureters at the bladder, and a proximal nerve bundle and sphincter at the urethral stump. All of these add up to a complicated and delicate suturing procedure that, if not performed properly, could result in complications such as leakage, difficulty in healing or failure to heal, incontinence, or impotence. Specific problems include necrosis of the sutured tissues; stricture of the urethra, which can impede the flow of fluid through it; and a urethra-bladder connection that is not fluid-tight. In addition, methods of suturing the urethra to the bladder allow for accidental or inadvertent piercing of the nearby neurovascular bundle, which can cause incontinence or impotence.

In order to overcome the problems associated with suturing during conventional prostatectomies, catheter-based anastomosis devices have been developed to provide a means by which the severed urethral stump and a severed bladder neck are retained and approximated throughout a healing period. These catheter-based anastomosis devices are available from American Medical Systems of Minnetonka, Minn. which is the assignee of the present application. Representative configurations and elements of these catheter-based anastomosis devices are described and illustrated within United States Patent Publication Nos. 2011/0118767, 2011/0288570, 2011/0295287 as well as U.S. Pat. Nos. 7,717,928, 7,771,443 and 8,066,725, all of which are herein incorporated by reference in their entirety.

SUMMARY OF THE INVENTION

The presently claimed invention relates to a urinary catheter that includes a catheter body having a clot prevention component at a distal treatment end. In some embodiments, the urinary catheter can comprise an anastomosis device that incorporates tissue approximation structure into the catheter body. The tissue approximating structure can be used to cause or maintain contact between severed portions of tissue to allow or cause the severed tissue surfaces to heal together, instead of using sutures. The device may be used, for example, in performing procedures such as a vesico-urethral anastomosis in association with a radical prostatectomy, or with an end-to-end urethral anastomosis. Advantageously, the device, including the tissue approximating structure, can be left installed during the healing process to function to allow the tissue to heal while at the same time functioning to drain urine from the bladder.

In one representative aspect of the present invention, a urinary catheter can include features and structures that function to drain the bladder, e.g., through a drainage lumen extending the length of the catheter body. In the case of the urinary catheter device comprising an anastomosis device, the drainage function can be performed simultaneously and in conjunction with a tissue approximating structure that retains and approximates severed tissue during a healing period. Representative methods of the present invention can use such an anastomosis device, including both a draining function and a tissue approximating function, to accomplish healing of the anastomosis, without sutures, and draining of the bladder, with the single anastomosis device and preferably without removing or replacing the device during or after the procedure until healing is complete. The anastomosis device can be installed during or after a radical prostate removal procedure, and can remain installed with the bladder-draining function and the tissue-approximating function in effect until the anastomosis is completely healed and the severed tissue, e.g., bladder and urethra, are re-connected. Thus, an advantage associated with inventive methods and devices can be that the anastomosis device performs dual functions when installed during and following an anastomosis procedure, of draining the bladder and functioning as a tissue approximating structure, at the same time.

Also advantageously, inventive methods and devices avoid the need to use sutures to connect severed tissue such as a bladder neck and urethral stump. The ability to avoid sutures provides very significant advantages of avoiding the potential for damage to surrounding tissues and nerves that can be caused by installation of sutures using a needle. Such damage can include, for example, damage to ureters at the bladder or damage to the sphincter or nerves located in the perineal floor. Damage to any of these tissues has the potential to cause incontinence or impotency. Additionally, installing sutures is a difficult and technique-sensitive process that must be performed in a confined space and that would be avoided if possible based on other alternatives. Thus, the invention offers the very significant advantage of eliminating the need to use sutures to re-attach severed tissues, and the attendant potential damage to those sensitive proximal tissues and nerves and the possibility of incontinence or impotency.

The terms "tissue approximating" and simply "approximating" refer to a process of bringing or holding body tissues in contact for healing. Examples include: the process of bringing severed surfaces of a bladder neck and a urethral stump, or two opposing severed urethral tissues, into contact for healing; and the process of holding severed surfaces of a bladder neck and a urethral stump, or two opposing severed urethral tissues, together for healing.

In one aspect of the present invention, a urinary catheter can comprise a catheter body having a proximal manipulation end, a distal treatment end and a drainage lumen that extends continuously between the proximal manipulation end and the distal treatment end. The urinary catheter can further comprise a clot prevention component mounted over the distal treatment end, such that the clot prevention component defines a plurality of entry points by which fluid can enter the drainage lumen. In one embodiment, the clot prevention component can comprise a flexible spring having a spring body defined by adjacent wound coils. The plurality of entry points can be continually defines between the adjacent wound coils. In some embodiments, the plurality of entry points can serve to filter and prevent large clots within the fluid from entering the drainage lumen. In some embodiments, flexing of the flexible spring can serve to break up these large clots into smaller sizes that are capable of being flushed from the drainage lumen without plugging or otherwise preventing fluid flow through the drainage lumen. In some embodiments, flexing of the flexible spring can be accomplished through movement of a patient or alternatively, a displacement device can be slidably advanced through the drainage lumen such that the displacement device physically contacts the spring body and mechanically forces the spring body to flex. In some embodiments, patient comfort can be improved by selectively winding the adjacent wound coils to vary a pitch of the spring body. The urinary catheter can further include tissue approximation structure so as to comprise an anastomosis device suited for use in a radical prostatectomy procedure.

In another aspect of the present invention, a method for preventing clotting of a urinary catheter can comprise providing a catheter body having a flexible spring mounted over a distal treatment end of the catheter body. The method can further comprise advancing the distal treatment end to a treatment location or other desired position within a patient's urinary tract. Finally, the method can comprise removing fluid by introducing the fluid into a drainage lument within the catheter body through a plurality of entry points defined between adjacent wound coils of the flexible spring. In some embodiments, the method can further comprise filtering the fluid with the flexible spring such that large clots are prevented from passing through the plurality of entry points and into the drainage lumen. In some embodiments, the method can further comprise breaking up large clots captured at the plurality of entry points by flexing the flexible spring. In some embodiments, the flexing of the flexible spring can be accomplished by movement of the patients, while in some embodiments, a displacement device can be advanced through the drainage lumen such that the displacement device contacts and flexes the flexible spring.

Another aspect of the device relates to an anastomosis device comprising a hollow, elongate, flexible catheter body having a proximal end and a distal end; an inflatable balloon at the distal end; a drainage lumen connected to the distal end; and tissue approximating structure on the catheter body on a proximal side of the balloon at a location to contact severed tissue during an anastomosis procedure.

Another aspect of the invention relates to a method of performing urethral anastomosis. The method comprises inserting a portion of an anastomosis device into the urethra, the anastomosis device comprising tissue approximating structure and a distal end comprising a balloon; inflating the balloon in the bladder; and using the tissue approximating structure to hold severed tissue together. Preferably, the device further comprises drainage apertures for draining a bladder and the method comprises draining a bladder.

Certain embodiments of the invention can include tissue approximating structure having one or more tines extending therefrom. The tines can be formed as sharp elongate, tubular straight or curved, or fine metal barbs that movably extend from the distal end of the catheter body at a location to facilitate contact and penetration of the urethral stump proximal tissue in the adjacent perineal floor, urethra, or bulbar urethra.

Still other embodiments can include one or more catheters configured to prevent the formation of blood clots and, thereby, improving the flow of urine out of the catheter. The catheter can include a spring device proximate the distal tip and catheter balloon. As a result, fluid flow through the catheter tip is improved by allowing for flow through the spaces between the adjacent coils of the spring device. Flexing of the spring during normal patient movement can also serve to break up clots (e.g., pinching of clots between adjacent coils). If the tip should become clogged, a stylet or other device can be inserted to stretch or displace the spring device or spring coils.

Further, the spring tip device can act as a filter which prevents large clots from entering the drainage lumen of the catheter. Patient comfort and fluid drainage can be enhanced by varying the flexibility of the spring along the length of the spring tip device. This can be accomplished by varying the pitch or other attributes of the spring device along its respective length.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be completely understood in consideration of the following detailed description of various embodiments of the invention in connection with the accompanying drawings, in which.

Figure 1:
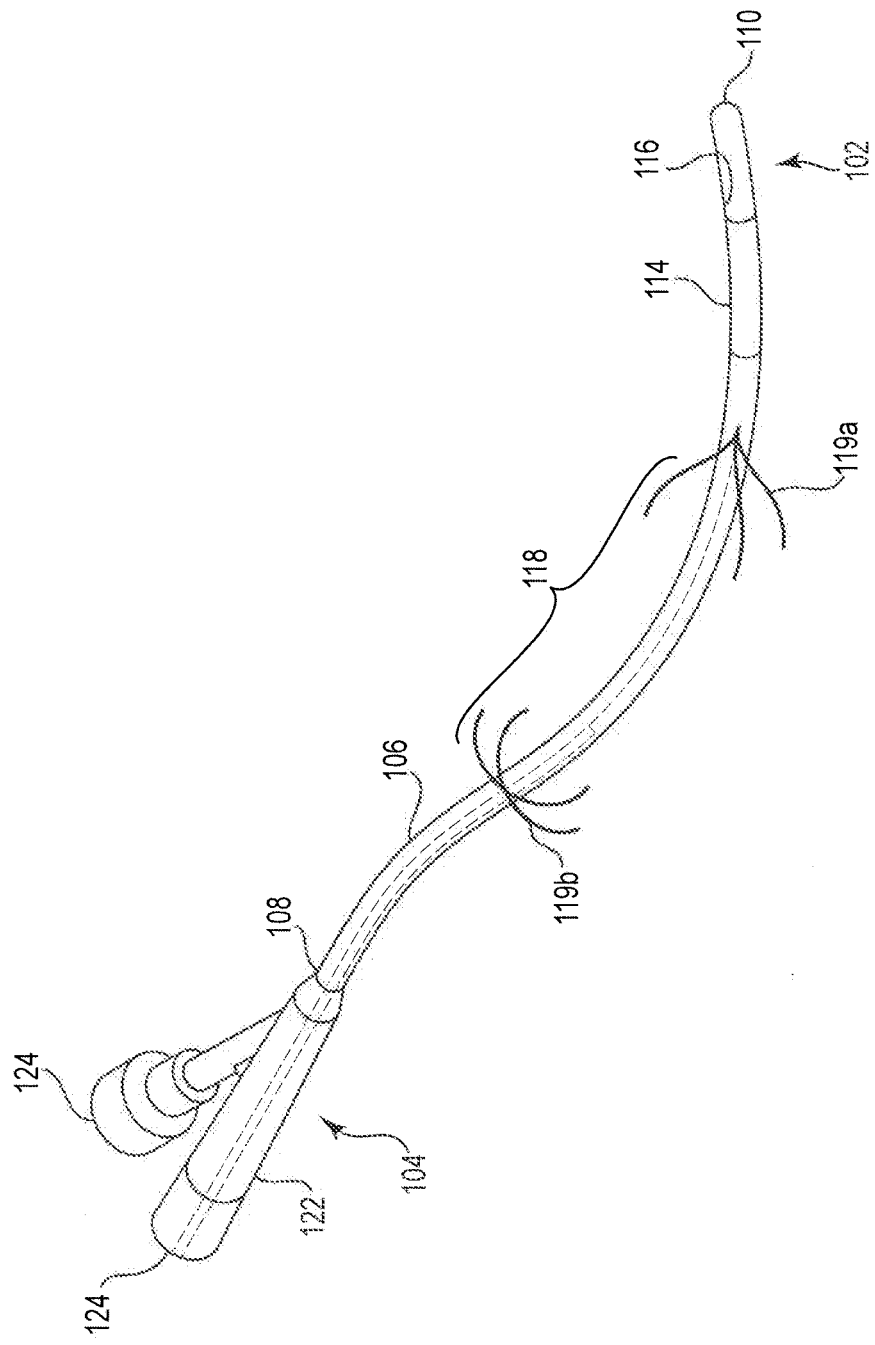
FIG. 1 is a perspective view of an anastomosis device of the prior art.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF PREFERRED EMBODIMENTS

Figure 2:
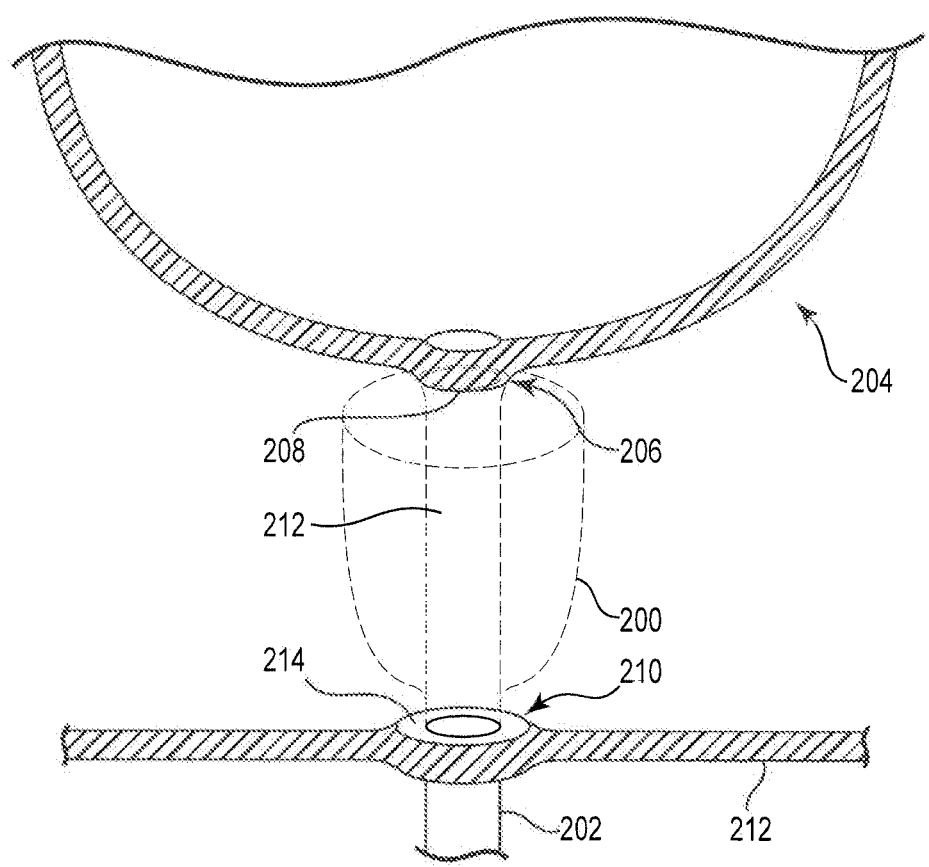
FIG. 2 is a schematic view to illustrate general aspects of radical prostate removal.
Figure 3:
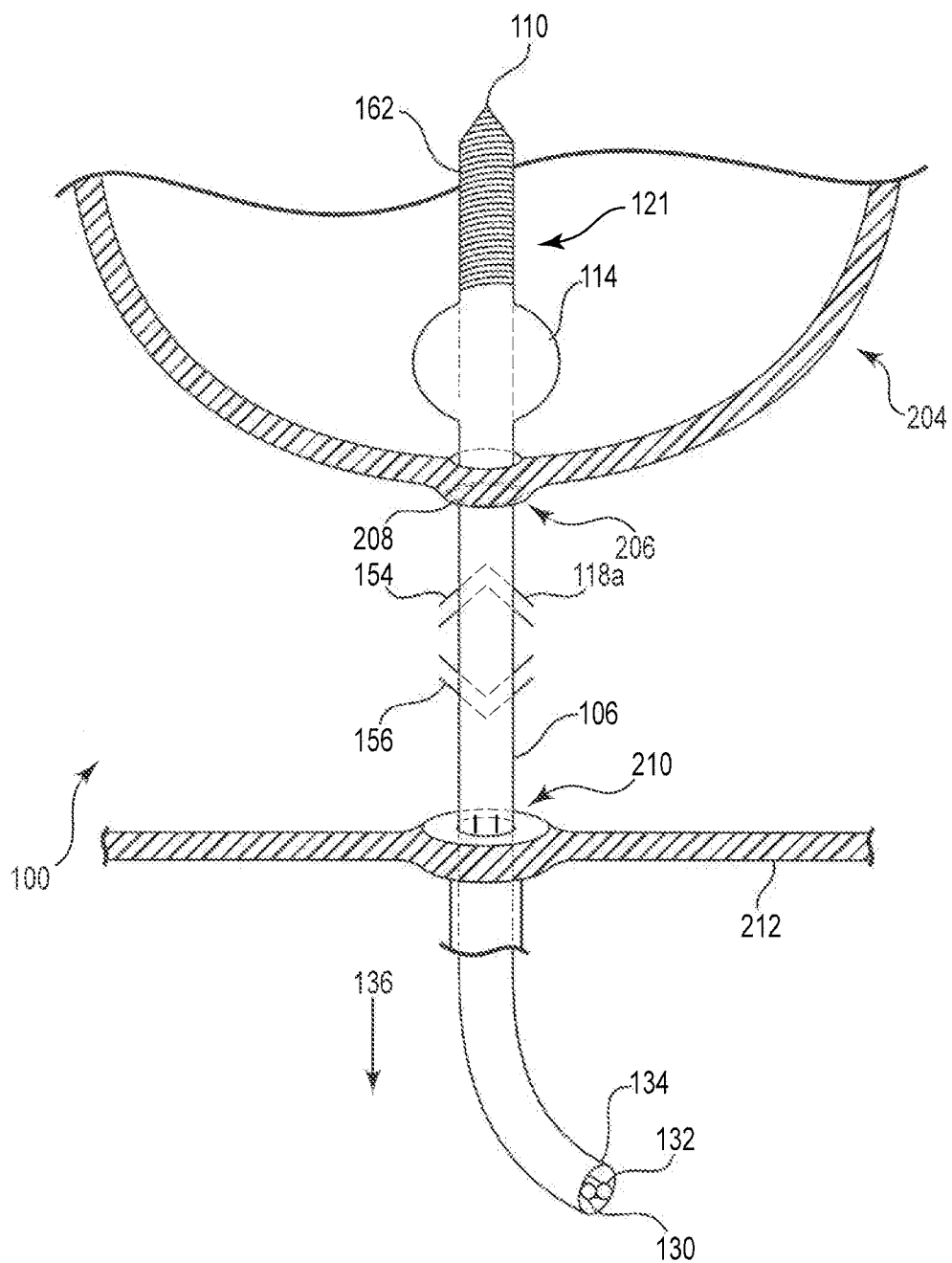
FIG. 3 is a schematic view of a portion of an anastomosis device in accordance with embodiments of the present invention.

Referring generally to FIGS. 1-3, an anastomosis device useful according to the invention can be any anastomosis device adapted to perform one or more of the methods described herein, e.g., an anastomosis method associated with a radical prostatectomy. An example of a useful design, generally, is the type sometimes referred to as a Foley catheter that has been constructed to include modified features as also presented in the present description including tissue approximating structure, ports, fluid conduits, and the like.

An anastomosis device of the invention can include a hollow, elongate, flexible catheter body having a proximal end and a distal end. An inflatable balloon can be located near the distal end, and an inflation lumen for inflating the balloon can extend to the balloon along the catheter body, e.g., along a portion or all of the catheter body from the proximal end to the balloon. During use, the balloon can rest against the neck of the bladder to prevent urine from entering the neck and to prevent urine from contacting the anastomosis site. Urine at the anastomosis site has the potential to cause difficulties in healing or to cause a stricture, among other deleterious effects. With the balloon blocking the bladder neck during use, urine will pool in the bladder and can be drained from the bladder, for example, using one or more draining apertures at the distal end of the anastomosis device connected to a drainage lumen. A drainage lumen can extend from one or more drainage apertures near the distal end, e.g., from apertures at the distal end to a location that is at or near the proximal end.

Overall, an anastomosis device can contain various lumens (e.g., for inflating a balloon, drainage, providing a fluid channel or conduit to the tines, for containing actuating mechanisms for tissue approximating structure, etc.) and actuating mechanisms running along at least a partial length of the catheter body. The mechanisms and lumens can be arranged in any useful adaptation, such as coaxially, side-by-side, or according to any other useful configuration. A lumen or a mechanism (e.g., actuating mechanism) that runs along at least a portion of the length of the catheter body may be diverted at the proximal end of the catheter body to a port that provides access to the lumen or mechanism during use. Further, the various devices, components, mechanisms, and methods disclosed in U.S. Patent Publication No. 2007/0219584 can be employed, alone or in combination, with the present invention and, therefore, the above-identified publication is incorporated herein by reference in its entirety.

Referring generally to FIG. 1, an anastomosis device 100 of the prior art can comprise a catheter portion 102 and an actuation portion 104. Catheter portion 102 generally comprises a catheter body 106 having a proximal connection portion 108 and a distal end portion 110. Catheter body 102 is generally constructed of a soft plastic or rubber tube. Located proximate to distal end portion 110, the catheter body can include an inflation balloon 114, a drainage aperture 116 and a tissue approximating structure 118. Tissue approximating structure 118 can comprise a single structure or multiple structures generally positioned along the catheter body 106 between the distal end portion 110 and the proximal connection portion 108. Tissue approximating structure 118 can include multiple sharp elongate tines 118a that can extend from and retract into catheter body 106 at a location that allows contact and optional penetration of adjacent tissue structures. Tissue approximation structure 118 can comprise a distalmost approximating structure 119a and a proximalmost approximating structure 119b.

Referring again to FIG. 1, proximal connection portion 108 of the anastomosis device 100 can operably connect to actuation portion 104 at an actuation body 122. Actuation body 122 generally possesses an increased diameter than catheter body 106. Actuation body 122 can include one or more ports 124 that extend or otherwise protrude from the actuation body 122 and generally provide access to distinct lumens defined within the catheter body 106 that can provide for inflation of the inflation balloon 114, drainage from the drainage aperture 116 or for control guidewires to operably connect to the tissue approximating structures 118.

According to embodiments of the invention, the anastomosis device can include tissue approximating structure that can be used to place or hold a cut or severed tissue or tissue surface in place for healing, as well as to inject or provide drugs or cell mixtures into target tissue to facilitate healing and overall tissue health. Referring generally to FIG. 2, a radical prostatectomy procedure includes removal of the prostate 200 (indicated in dashes) and urethra 202 (also in dashes), leaving bladder 204 with bladder neck 206 having a severed tissue surface 208 at one end of removed urethra 202, and a urethral stump 210 extending from perineal floor 212, with urethral stump 210 having severed tissue surface 214 opposing the severed tissue surface 208 of bladder neck 206. While the following description presents inventive devices and methods primarily in the context of vesico-urethral anastomosis relating to radical prostatectomy, it will be apparent that the invention can be applied to a variety of other procedures that benefit from tissue approximating structures and in particular where a fluid flow is also desired, such as drainage of urine. A specific example is an end-to-end urethral anastomosis procedure.

Tissue approximating structure 118 according to the invention can be a structure of the device that can be used to cause contact between severed tissues, such as severed urethral tissues, or such as severed tissue of the bladder or bladder neck with severed tissue of the urethral stump or perineal floor, or alternatively or additionally to hold severed tissue surfaces in contact with each other for healing. The tissue approximating structure may include, for example, one or multiple inflation balloon 114 or balloon-like structures that can be placed against the inside of the bladder or underneath the perineal floor to bring the severed bladder neck tissue into contact with the severed tissue surface of the urethral stump. The tissue approximating structure may further include elongate structures such as needles or tines 118a (solid or hollow), prods, probes, or the like, which may have a blunt or a sharp end and may selectively extend or protrude from an aperture in a flexible catheter body at a location where the structure can function as an approximating structure, e.g., at the distal end portion 110 of the anastomosis device 100 where the structure will be near the bladder or perineal wall (when installed), or at a severed urethra below the perineal floor (when installed). Combinations of balloons and elongate structures may also be useful in certain applications. The tissue approximating structure 188 does not require and can specifically exclude and/or replace sutures.

An example of a useful tissue approximating structure 118 can be in the form of a sharp or blunt elongate structure (e.g., a sharp-ended needle or tine) that can be movably extended from an aperture at a distal portion of, or along a length of, the catheter body 106, to thereby contact and optionally penetrate into or through one or more of a tissue of the bladder, bladder neck, urethra, bulbar urethra, urethral stump, or perineal floor. These structures can serve to place opposing severed tissue surface into contact for healing, and preferably also to hold the tissues in contact with each other during the healing period. Certain embodiments of the invention can include sharp or blunt elongate tissue approximating structure 118 (e.g., a sharp-ended needle or tine 118a) that can be movably extended from an aperture at a distal end of a catheter body to place opposing severed tissue of the bladder neck into contact with a severed tissue surface of the urethral stump, or vice versa, and preferably also to hold the tissues in contact with each other during the healing period.

Referring to FIG. 3, prostate 200 has been removed to leave a severed urethral stump tissue 210 and opposing severed bladder neck 206. Anastomosis device 100 is installed through urethral stump 210 and bladder neck 206. The device 100 comprises catheter body 106 and inflation balloon 114 located at the distal end portion 110 of the anastomosis device 100. As shown, anastomosis device can also include a drainage lumen 130, an actuation lumen 132 and one or more inflation lumens 134. Drain aperture 116 is generally located between the distal end portion 116 of the anastomosis device 100 and inflation balloon 114. Inflation balloon 114 is inflated, after insertion into the bladder 204, by a flow of fluid through inflation lumen 134. Pressure (e.g., traction as shown by arrow 136) can then be applied through the length of anastomosis device 100 to produce a pressure against the inside of bladder 204 from inflated inflation balloon 114.

In related embodiments of devices according to FIGS. 1-3, the anastomosis device 100, which can include the inflation balloon 114 as a tissue approximating structure 118, can also include additional components or features as part of the tissue approximating structure, including a plurality of (or at least one) injection needles or tines 118a. A set of distalmost tines 154 and proximalmost tines 156 can reside within the catheter body 106 prior to deployment during an anastomosis procedure. The tines 118a can include a lumen or channel therethrough, such that the tines are in fluid communication with the one or more conduits or ports. The conduits can include a plurality of fluid lines each provided in separate communication with respective tines, or a single conduit can be included in communication with one or more groupings of tines (e.g., single conduit to distalmost tines 154, with another conduit to proximalmost tines 156). Various other fluid channeling and configurations are envisioned for use with the present invention. It is noted that various other catheter, conduit, port and tine configurations can be employed to facilitate introduction of drugs or cells into target tissue via needles or tines to provide local or site-specific delivery.

Figure 4:
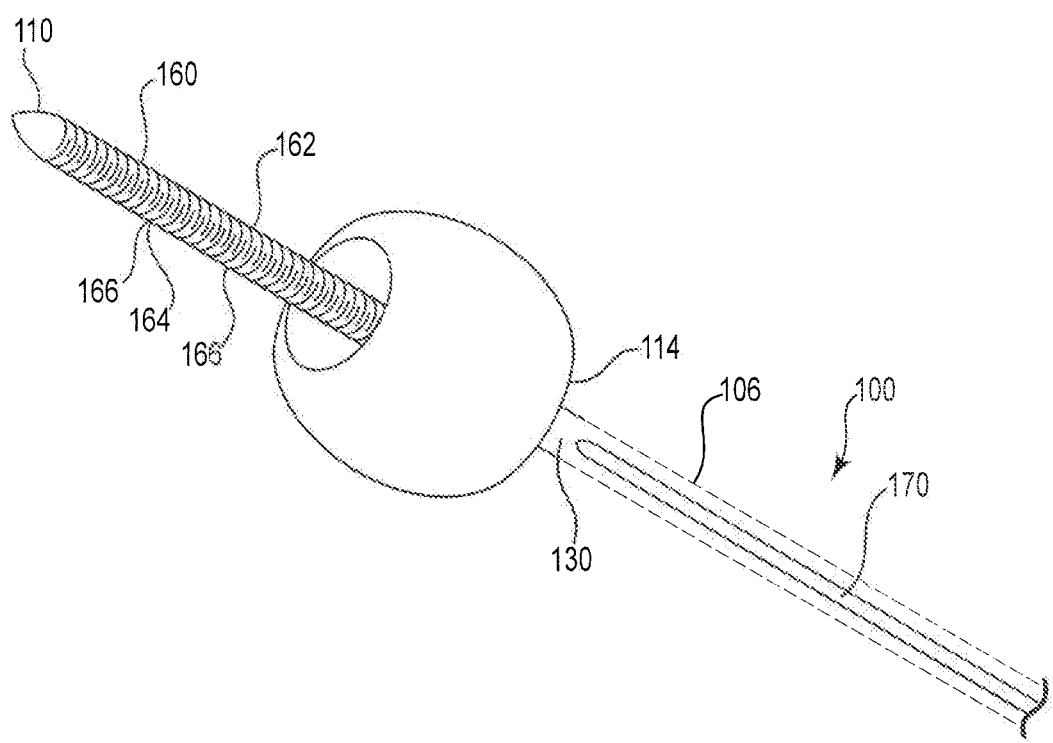
FIG. 4 is a schematic view of a distal portion of an anastomosis device, showing a distal spring device, in accordance with embodiments of the present invention.

In various embodiments, as shown in FIGS. 3 and 4, the distal end portion 110 can include a clot prevention component 160 including an extending spring tip device 162 mounted over the drainage aperture 116. Such embodiments, with or without approximation features, are provided to prevent the formation of blood clots and, thereby, improving the flow of urine out of the catheter. The spring tip device 162 can be provided proximate the inflation balloon 114. As a result, fluid flow through the drainage aperture 116 is improved by allowing for flow through open spaces 164 between adjacent coils 166 of the spring tip device 162. Flexing of the spring tip device 162 during normal patient movement can also serve to break up clots (e.g., pinching of clots between adjacent coils). If the spring tip device 162 should become clogged, a stylet 170 or other similar device can be inserted along through the drainage lumen 130 of the catheter body 106 to stretch or displace the adjacent coils 166 of the spring tip device 162.

Further, the spring tip device 162 can act as a filter which prevents large clots from entering the drainage lumen 130 of the catheter body 106. Patient comfort and fluid drainage can be enhanced by varying the flexibility of the spring along the length of the spring tip device 162. This can be accomplished by varying the pitch or other attributes of the adjacent coils 1622 along the length of the spring tip device 162.

The catheter and its componentry may be made of materials normally used and known to be useful for such devices, including relatively inert and biocompatible materials. For example, a catheter body may be prepared from a flexible plastic or polymeric material. Examples of materials that may be useful for a catheter body can include silicones, latex, rubbers, polyurethanes, and combinations of these or other materials. A tissue approximating structure can be made from these or other materials, including relatively rigid plastics, polymers, or metals, optionally including bioresorbable materials such as bioresorbable polymers. Examples of metals include stainless steel, nitinol, titanium, tantalum, as well as alloys or combinations of these materials.

In general, a catheter can be used during urethral anastomosis procedures such as that associated with a radical prostatectomy, e.g., vesico-urethral anastomosis, with the catheter functioning to remove urine from the bladder after the procedure. The anastomosis device can be used by inserting the elongate flexible catheter body through the urethra and into the bladder. A portion of the distal end of the device becomes located inside of the bladder where the balloon can be inflated and where the drainage lumen can be used to drain the bladder and keep urine out of the bladder during and subsequent to the procedure. The bladder can preferably be drained of urine during the procedure and during the healing period following the procedure, because urine is preferably kept away from the site of anastomosis to facilitate healing, and also to prevent urine from creating pressure within the bladder.

Certain embodiments can include various drugs and/or cellular mixtures, e.g., cells and adipose tissue, coated onto, or impregnated or otherwise provided with structures of the device. Again, these structures can come into contact with target tissue to increase the speed and degree of healing, and to promote overall tissue health. For instance, the tines or distal tip, with or without fluid injection capabilities, can include the cellular mixtures. In other embodiments, foam wrappings, protrusions, or surface portions of the device can include the drugs and/or cellular mixtures.

Generally, a method of the invention can include a step of performing a radical prostatectomy, such as by a retropubic technique, a laparoscopic technique, or a transperineal technique. These techniques leave a bladder neck and a urethral stump for re-attachment. The distal portion of the anastomosis device may optionally be partially installed during the prostatectomy procedure, e.g., up to the perineal floor, or may be installed to that point afterward. Following removal of the prostate, the catheter body of the distal end of the device is passed through the urethral stump and then through the bladder neck. From there, the technique can include inflating the balloon inside of the bladder, using tissue approximating structure (including tines 54, 46) to place the severed tissue surfaces of the urethral stump and the bladder neck into contact, and injecting drugs or cells (such as a cell mixture) into the target tissue through the engaged injection tines.

All patents, patent applications, and publications cited herein are hereby incorporated by reference in their entirety as if individually incorporated, and include those references incorporated within the identified patents, patent applications and publications.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative embodiments.

The invention claimed is:

1. A urinary catheter, comprising:
   a catheter body having a proximal manipulation end and a distal treatment end, the catheter body including a drainage lumen defined between the proximal manipulation end and the distal treatment end, the catheter body further including a drainage aperture proximate the distal treatment end, the drainage aperture being fluidly connected to the drainage lumen; and
   a clot prevention component mounted over the distal treatment end so as to cover the drainage aperture, the clot prevention component including a spring device including a spring body formed by a plurality of wound coils in adjacent relation, the entry points defined as spaces between adjacent wound coils, whereby a fluid can simultaneously enter the drainage aperture via the plurality of entry points, and whereby the fluid flows through the drainage lumen for removal of the fluid at the proximal manipulation end.

2. The urinary catheter device of claim 1, wherein the spring device comprises a flexible spring device, wherein patient movement can result in flexing of the spring body, whereby clots formed between adjacent wound coils are broken up by relative movement between the adjacent wound coils.

3. The urinary catheter device of claim 2, wherein a pitch of the adjacent wound coils varies along a length of the spring body.

4. The urinary catheter device of claim 1, further comprising:
   a displacement device including a displacement body, a displacement tip and a displacement manipulation end, wherein said displacement body is slidably insertable into the drainage lumen whereby the displacement tip can be directed into contact with the spring body to stretch or otherwise displace the adjacent wound coils.

5. The urinary catheter device of claim 1, wherein the adjacent wound coils along the spring body define a fluid filter preventing large clots from entering the drainage lumen.

6. An anastomosis device for use in a radical prostatectomy procedure, comprising:
   a catheter body having a proximal manipulation end and a distal treatment end, the catheter body including a drainage lumen defined between the proximal manipulation end and the distal treatment end, the catheter body further including a drainage aperture proximate the distal treatment end, the drainage aperture being fluidly connected to the drainage lumen; and
   a flexible spring mounted over the distal treatment end so as to cover the drainage aperture, the flexible spring including a spring body defined by a plurality of adjacent wound coils, wherein a plurality of fluid entry points are defined along the spring body between adjacent wound coils, wherein a fluid enters the drainage aperture through the plurality of fluid entry points, whereby the fluid flows through the drainage lumen for removal of the fluid at the proximal manipulation end.

7. The anastomosis device of claim 6, wherein the plurality of adjacent wound coils define a fluid filter to prevent large clots from entering the drainage lumen.

8. The anastomosis device of claim 7, wherein flexing of the spring body breaks up large clots captured by the plurality of entry spaces.

9. The anastomosis device of claim 8, wherein a displacement device including a displacement tip is slidably insertable into and through the drainage lumen whereby the displacement tip can be directed into contact with the spring body to flex the spring body.

10. The anastomosis device of claim 6, wherein a pitch of the adjacent wound coils varies along a length of the spring body.

11. A method for preventing clotting of a urinary catheter, comprising:
    providing a catheter body having a flexible spring mounted over a drainage aperture located at a distal treatment end of the catheter body, the flexible spring having a spring body formed by a plurality of adjacently wound coils wherein fluid entry points are continuously defined between the adjacently wound coils;
    advancing the distal treatment end to a desired location within a patient's urinary tract; and
    removing fluid from the desired location by introducing the fluid through the fluid entry points and into the drainage aperture, the drainage aperture fluidly connected to a drainage lumen within the catheter body that is fluidly connected to a proximal manipulation end.

12. The method of claim 11, further comprising:
    filtering the fluid with the flexible spring such that large clots are prevented from passing through the fluid entry points.

13. The method of claim 12, further comprising:
    flexing the spring body to break up large clots captured by the fluid entry points.

14. The method of claim 13, wherein flexing the spring body, comprises:
    advancing a displacement device through the drainage lumen whereby the displacement device is directed into contact with the flexible spring to flex the spring body.

15. The method of claim 12, wherein the flexing of the spring body is a result of patient movement.

* * * * *